(12) United States Patent
Halg et al.

(10) Patent No.: US 7,247,483 B2
(45) Date of Patent: Jul. 24, 2007

(54) METHOD FOR DETERMINING THE VOLUME OF A LIQUID SAMPLE

(75) Inventors: Werner Halg, Mannedorf (CH); Nikolaus Ingenhoven, Mannedorf (CH); Michael Trosch, Hombrechtikon (CH)

(73) Assignee: Tecan Trading AG, Baar (CH)

( * ) Notice: Subject to any disclaimer, the term of this patent is extended or adjusted under 35 U.S.C. 154(b) by 547 days.

(21) Appl. No.: 09/992,313

(22) Filed: Nov. 19, 2001

(65) Prior Publication Data

US 2002/0149772 A1    Oct. 17, 2002

(30) Foreign Application Priority Data

Nov. 17, 2000  (CH)  .............................. 2000 2252/00
Nov. 23, 2000  (CH)  .............................. 2000 2281/00

(51) Int. Cl.
*G01N 31/00*   (2006.01)
*G01N 21/00*   (2006.01)
*G01N 33/20*   (2006.01)

(52) U.S. Cl. .............................. 436/8; 436/10; 436/164; 436/76; 436/84

(58) Field of Classification Search .................... 436/8, 436/10, 164, 166, 179, 180, 76, 84
See application file for complete search history.

(56) References Cited

U.S. PATENT DOCUMENTS

| 4,354,376 A | 10/1982 | Greenfield et al. |
| 5,061,639 A * | 10/1991 | Lung et al. .................. 436/164 |
| 5,298,978 A * | 3/1994 | Curtis et al. .................. 356/627 |
| 5,320,969 A * | 6/1994 | Bauer et al. .................. 436/84 |
| 5,492,673 A * | 2/1996 | Curtis et al. .................. 422/61 |

FOREIGN PATENT DOCUMENTS

| EP | 0 431 578 | 6/1991 |
| WO | WO 95/02166 | 1/1995 |

OTHER PUBLICATIONS

Article by Joel P. Schneider and Jeffrey W. Kelly titled, "Synthesis and Efficacy of Square Planar Copper Complexes Designed to Nucleate β-Sheet Structure," Sep. 19, 1994, Journal of American Chemical Society, vol. 117, No. 9, 1995.

(Continued)

*Primary Examiner*—Brian R. Gordon
(74) *Attorney, Agent, or Firm*—Frommer Lawrence & Haug; Thomas J. Kowalski; Deborah L. Lu

(57) ABSTRACT

A method, a device, and a test kit for performing this method for determining the volume of a sample of the liquid. In the method, a specific concentration of a chromophoric indicator is provided in this liquid, a sample is separated from the liquid, the optical absorption of the separated sample is measured, and the volume of the separated sample is determined by correlation of the measured optical absorption with the concentration of indicator in this liquid. Ions that generate a color in the sample by complexing with a specific ligand are used as the indicator to stain the liquid.

23 Claims, 3 Drawing Sheets

OTHER PUBLICATIONS

Article by Chuluo Yang et al., titled, "Synthesis and third-order optical nonlinearity of some salts comprising planar pomplex cation and anion," undated, Synthetic Metals 120 (2001) 789-790.

Article by L. Edward Godycki and R.E. Rundle titled, "The Structure of Nickel Dimethylglyoxime," Received Oct. 15, 1952, Acta Cryst. (1953).

Article by John Oakes, Gordon Welch and Peter Gratton titled, "Kinetic investigations into the copper (II)-catalysed peroxosulfate oxidation of Calmagite dye in alkaline media" undated, J. Chem. Soc., Dalton Trans., 1997.

* cited by examiner

METHOD FOR DETERMINING THE VOLUME OF A LIQUID SAMPLE

This application claims priority under 35 U.S.C. §119 to Swiss patent application 2000 2252/00, filed Nov. 17, 2000 and Swiss patent application 2000 2281/00, filed Nov. 23, 2000.

FIELD OF THE INVENTION

The present invention relates to a method for determining the volume of a sample of a liquid (A), wherein, in order to stain the liquid (A), a specific concentration of a chromophoric indicator is provided in this liquid (A), a sample is separated from the liquid (A), the optical absorption of the separated sample is measured, and the volume of the separated sample is determined by correlation of the measured optical absorption with the concentration of indicator in this liquid (A).

BACKGROUND OF THE INVENTION

It is known that droplets with a volume of more than 10 µl can be dispensed from the air very easily, since if the pipette is correctly manipulated, the droplets leave the pipette tip of their own accord. The droplet size is then determined by the physical properties of the sample liquid, such as surface tension or viscosity. The droplet size thus limits the resolution of the quantity of liquid to be dispensed.

The aspirating and dispensing, i.e. the pipetting of liquid samples with a volume of less than 10 µl, in contrast, typically requires instruments and techniques which guarantee the dispensing of such small samples. The dispensing of a liquid with a pipette tip, i.e. with the endpiece of a device for aspirating and/or dispensing sample liquid, can occur from the air ("from air") or by touching a surface. This surface can be the solid surface of a container ("on tip touch"), into which the liquid sample is to be dispensed. It can also be the surface of a liquid in this container ("on liquid surface"). A mixing procedure following the dispensing is recommended—particularly for very small sample volumes in the nanoliter or even picoliter range—so that uniform distribution of the sample volume in a diluent is ensured.

Systems for separating samples from a liquid are known as pipettors. Such systems serve, for example, for dispensing liquids into the wells of Standard Microtitration Plates™ (trademark of Beckman Coulter, Inc., 4300 N. Harbour Blvd., P.O. Box 3100 Fullerton, Cailf., USA 92834) and/or microplates with 96 wells. The reduction of the sample volumes (e.g. for filling high-density microplates with 384, 864, 1536, or even more wells) plays an increasingly important role, with the precision of the sample volume dispensed being of great importance. The elevation of the number of samples typically also requires miniaturization of the experiment, so that the use of a pipettor is necessary and special requirements must be placed on the precision of sample volumes and the accuracy of the movement control and/or of the dispensing of this pipettor.

Disposable tips significantly reduce the danger of unintentional transfer of parts of the sample (contamination). Simple disposable tips are known (so-called "air-displacement tips"), whose geometry and material is optimized for the exact aspirating and/or dispensing of very small volumes. The use of so-called "positive-displacement tips", which have a pump plunger inside, is also known.

For automation, two procedures must be differentiated from one another: the defined aspiration and the subsequent dispensing of liquid samples. Between these procedures, typically the pipette tip is moved by the experimenter or by a robot, so that the aspiration location of a liquid sample is different from its dispensing location. For the precision of dispensing and/or aspiration/dispensing, only the liquid system is essential, which comprises a pump (e.g. a diluter implemented as a syringe pump), tubing, and an endpiece (pipette tip).

The precision (ACC=accuracy) and reproducibility (CV=coefficient of variation) of the dispensing and/or aspiration/dispensing of a liquid sample can be influenced by greatly varying parameters. The speed of dispensing largely determines, for example, how the droplet breaks away from the pipette tip.

In principle, two basic modes are differentiated in pipetting: single pipetting and multipipetting. In the single pipetting mode, a liquid sample is aspirated and dispensed at another location. In the multipipetting mode, a larger volume of liquid is aspirated at one time and subsequently dispensed in several—typically equivalent—portions (aliquots) at one or more different locations, e.g. in various wells of a Standard Microtitration Plate™.

The measurement of the volume of a liquid sample, however, does not take into consideration the way in which a droplet was separated: in Europe, the norm ISO/DIS 8655-1 of the International Organization for Standardization (ISO) (whose main offices are in Geneva, Switzerland) has been available at least in draft form since 1990. This norm defines the basic conditions for performing laboratory work with dispensing devices, such as pipettes, dispensers, and burettes. Known national norms, such as ASTM (USA), British Standard (GB), or the newest draft DIN 12650 (Germany), have to fit themselves into the system of the ISO norm ISO/DIS 8655-1.

The norm DIN 12650 essentially differentiates two methodical categories for testing measurement accuracy of dispensers in its 4th draft from 1996. These are the gravimetric and non-gravimetric methods. Since not every laboratory has available sufficient balanced weighing stations and costly scales with the necessary resolution (six decimal places) for performing gravimetric measurements, photometric tests for hand pipettes, e.g. for the range of sample volumes from 0.2 to 1 µl, have been offered by the industry (e.g. the firm EPPENDORF AG, Barkhausenweg 1, D-22339 Hamburg, Germany).

A further method is known from the article "Performance Verification of Small Volume Mechanical Action Pipettes" by Richard H. Curtis [Cal.Lab, May/June 1996]. In consideration of the difficulties (e.g. evaporation, vibrations, static charge of the samples) of the application of gravimetric methods to a liquid sample in the microliter range, in this article an integrated system was suggested based on using calorimetric substances. However, the concentration of indicator substance whose optical density is to be measured must be known exactly. This optical density is calculated as $\log_{10}(1/T)$, with T referred to as transmittance. This transmittance corresponds to $I/I_0$, i.e. the ratio of output intensity and input intensity of the light beams penetrating the sample. Furthermore, the device used for measuring the optical density must also meet international norms. In addition, problems such as a dependence of the measurement on the sample temperature, the appearance of changes in the solution, and the appearance of wear in the measurement cuvette must be considered. The firm ARTEL Inc., 25 Bradley Drive Westbrook, Me., USA, produces the "Artel PCS™ Pipette Calibration System" of this type. It essentially consists of a prefilled, sealed test glass with 4.75 ml of an exactly defined concentration of a copper chloride solution and an instrument for measuring the optical absorption (wherein optical absorption $A=I_0/I=-\log_{10} T$) of this solution at a wavelength of 730 nm. The test glass is inserted in the instrument and remains in place during the entire calibration process. The experimenter opens the seal of the test glass and adds a sample corresponding to the desired measurement precision to the glass with the pipette to be checked, and then reseals the seal. The sample added is a solution of "Ponceau S", an organic test substance, which, among other things, is selected due to its long-term stability and good "pipettability" (similar to water, even at high concentrations) and its wide, well-defined absorption peak at 520 nm. The absorption peaks of the copper chloride solution and of the test solution "Ponceau S" do not overlap. In addition, the test solution contains biocides, in order to prevent the growth of microorganisms, and a pH-stabilizing buffer. The device mixes the two solutions with an integrated mixer and determines the absorption at 520 nm (Ponceau S) and at 730 nm (copper chloride). The volume of the sample added is then calculated on the basis of these two measured values and the known initial concentrations. Although this system has the advantage that the measurement of the optical absorption is allowed independently of the path length and irregularities in the test glass, it nonetheless has the disadvantage that it cannot be adapted at a reasonable expense for usage in a multichannel pipetting robot.

A further calibration method of this type uses "Orange G" as the test substance, which allows an absorption measurement with high sensitivity. However, it is disadvantageous in this case that the flat molecules of this test substance have a high adhesion to the inner walls of the pipette tip and/or to the tubings, troughs, and/or wells of microplates. Therefore, an uncontrollable reduction of the Orange G concentration in the test liquid occurs, which makes the reliability of the test questionable.

Another method of this type is known from Belgian patent No. BE 761 537, which describes the analysis of various substances with increased precision, particularly automatic analysis, which depends on the sample volume of the substance. According to this invention, one mixes chromium in the form of $Cr_2(SO_4)_3 \cdot 10H_2O$ into a sample as an indicator, in order to obtain a specific concentration of chromium (III) therein. With reference to the chromium (III) concentration measured, the effective volume of the sample is calculated. The sample volumes are in the milliliter range. $Cr_2(SO_4)_3 \cdot 10H_2O$ exists in aqueous solution as $[Cr(H_2O)_6]^{3+}$. According to the literature (see, for example, W. Schneider in "Einführung in die Koordinationschemie", Springer Verlag Berlin, Heidelberg, New York 1968, pp. 115-117), the aqueous complex $[Cr(H_2O)_6]^{3+}$ has a molar extinction coefficient ($\epsilon$) of only approximately 13 (where an $\epsilon$ of less than 100 is a low to average value). In pure aqueous complexes, the extinction coefficient $\epsilon$ is approximately 50. The concentration of a pigment and the optical absorption are linked via the Beer-Lambert law $$A=c*\epsilon*l.$$

where:

A=optical absorption c=concentration of the dissolved material [M=Mol/L]

$\epsilon$=molar extinction coefficient of the dissolved material [1/(M·cm)]

l=layer thickness (the liquid which the light must pass through) [cm].

Due to limitations in spectrophotometric hardware reasons, the art (cf. Bruno Lange et al. in "Photometrische Analyse", VCH Verlagsgesellschaft mbH, Weinheim, 1987, p. 21) recommends that measurements only be performed in the absorption range from 0.1 to 1. The sensitivity of the measurement system increases with higher $\epsilon$. In order to be able to measure a volume of 1 µl in a final volume of 200 µl with an optical absorption of 0.1, the concentration of $[Cr(H_2O)_6]^{3+}$ must be at least 15 Mol/L according to the Beer-Lambert law. However, the physical properties of the sample are significantly changed by these high concentrations, and this, of course, is undesirable.

SUMMARY OF THE INVENTION

The object of the present invention is to provide an alternative method and a corresponding device for determining the volume of a sample of a liquid that eliminates the inadequacies from the prior art and allows calibration even in the sub-microliter range.

In one embodiment, there is provided a method for determining the volume of a dispensed liquid sample, comprising the steps of providing a volume of a diluent in a container; dispensing a liquid sample into said diluent in the container; mixing the dispensed liquid sample with said diluent in the container; staining of said mixture in the container by adding a chromophoric indicator; measuring the optical absorption of said stained mixture in the container; and determining the volume of the dispensed liquid sample by correlating said measured optical absorption of the mixture with the optical absorption of a test sample that has an exactly defined concentration of the same chromophoric indicator, wherein the chromophoric indicator to stain the mixture of sample liquid and diluent is formed by complexing indicator ions with chromogenic ligands comprising the liquid sample.

In another embodiment, there is provided a method for determining a residual volume of a liquid in a sample holder, which had been provided with a liquid and from which a part of the liquid has been removed, so that only said residual volume of the liquid remains in the sample holder, the method comprising the steps of adding a chromophoric indicator to said liquid to achieve a specific concentration of said indicator and thereby speeific staining of the liquid; removing a part from said stained liquid in the sample holder; adding a diluent to the stained residual volume of the liquid; measuring the optical absorption of the diluted residual volume of the liquid; and determining the residual volume of the liquid by correlating the measured optical absorption of the diluted residual volume of the liquid with the optical absorption of a test sample that has the same specific concentration of the chromophoric indicator, wherein the chromophoric indicator to stain the liquid is formed by complexing indicator ions with chromogenic ligands.

Additional and/or refining features arise from the dependent claims.

The metal complex pigments used according to the present invention have extinction coefficients $\epsilon$ of more than 10,000, which, when compared to the prior art, permits significantly more sensitive measurement systems to be used. For example, iron-tris-bathophenantroline-disulfonic acid disodium complex $[Fe(C_{24}H_{16}N_2O_6S_2)_3]^{4-}$ has an $\epsilon$ of approximately 18,700 (at 532 nm), while the iron-trisferrozine complex $[Fe(C_{20}H_{12}N_4O_6S_2)_3]^{4-}$ has an $\epsilon$ of approximately 22,000 (at 560 nm), the copper Chromazurol S complex $[Cu(C_{23}H_{13}Cl_2O_9S]^-$ has an $\epsilon$ of approximately 16,000 (at 522 nm), and the copper-bis-bathophenantroline-disulfonic acid disodium complex $[Cu(C_{24}H_{16}N_2O_6S_2)_2]^{3-}$ has an $\epsilon$ of approximately 13,800 (at 481 nm).

Intensively colored organic pigments known in the prior art (typically large conjugated Π-system are, in principle, planar (e.g. Orange G). Due to this planarity, they have a disadvantageous high affinity, caused by the Van der Waals forces, for apolar surfaces such as the inner walls of the pipette tip, of the tubing, or of the well.

BRIEF DESCRIPTION OF THE DRAWINGS

An example of a molecule from the prior art is shown in FIG. 1 and two examples of metal complex pigments as provided herein for use in the method according to the present invention for determining the volume of the sample of a liquid are shown in FIGS. 2 and 3.

FIG. 1 shows Orange G
FIG. 2 shows copper(I)-bis-(bathophenantroline-disulfonic acid disodium) complex
FIG. 3 shows iron(II)-tris(ferrozine) complex

DETAILED DESCRIPTION OF THE INVENTION

Figure 1A:
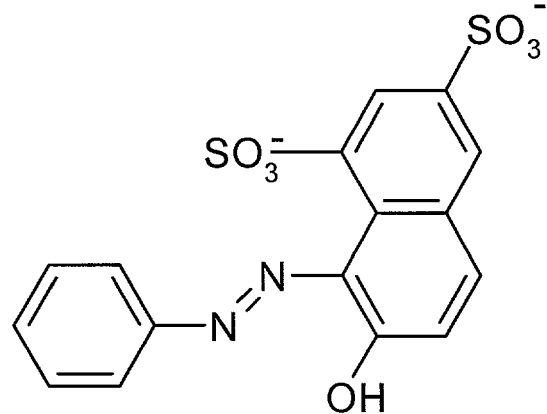
FIG. 1a shows the structural formula
Figure 1B:
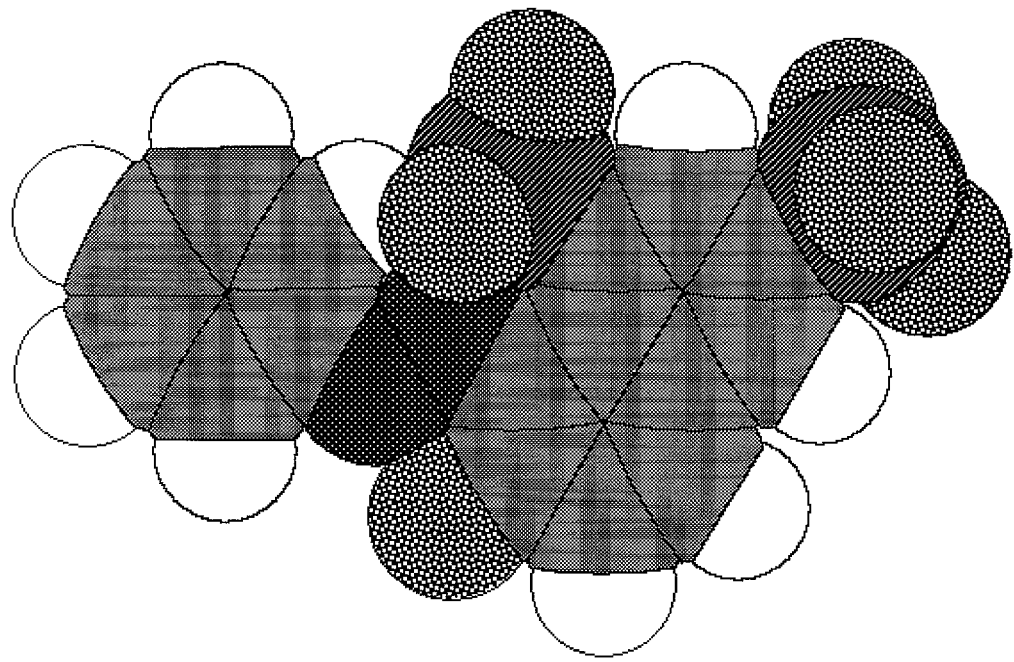
FIG. 1b shows a horizontal projection, space-filling
Figure 1C:
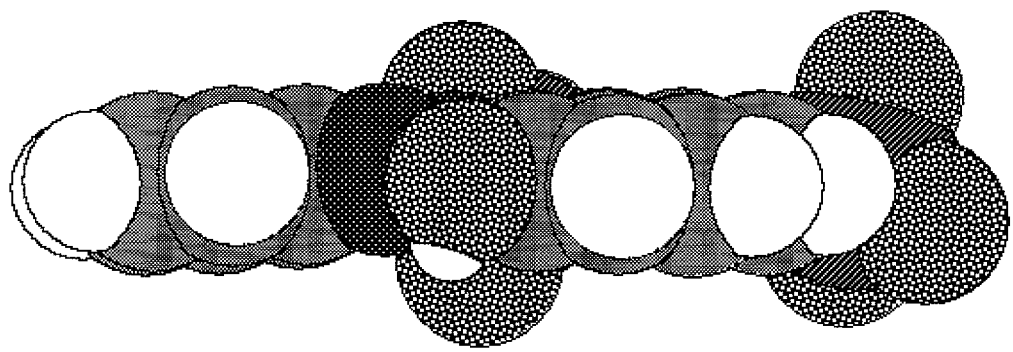
FIG. 1c shows a side view, space-filling
Figure 2A:
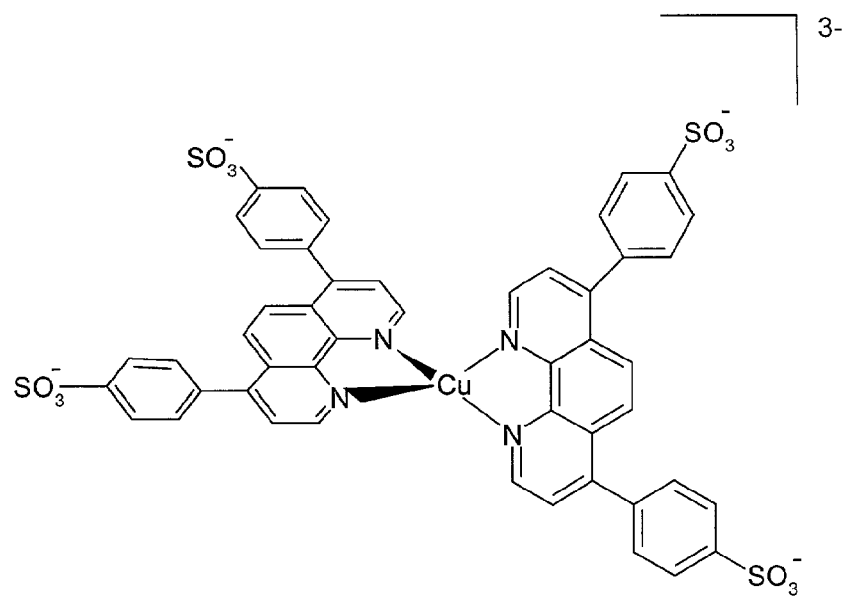
FIG. 2a shows the structural formula
Figure 2B:
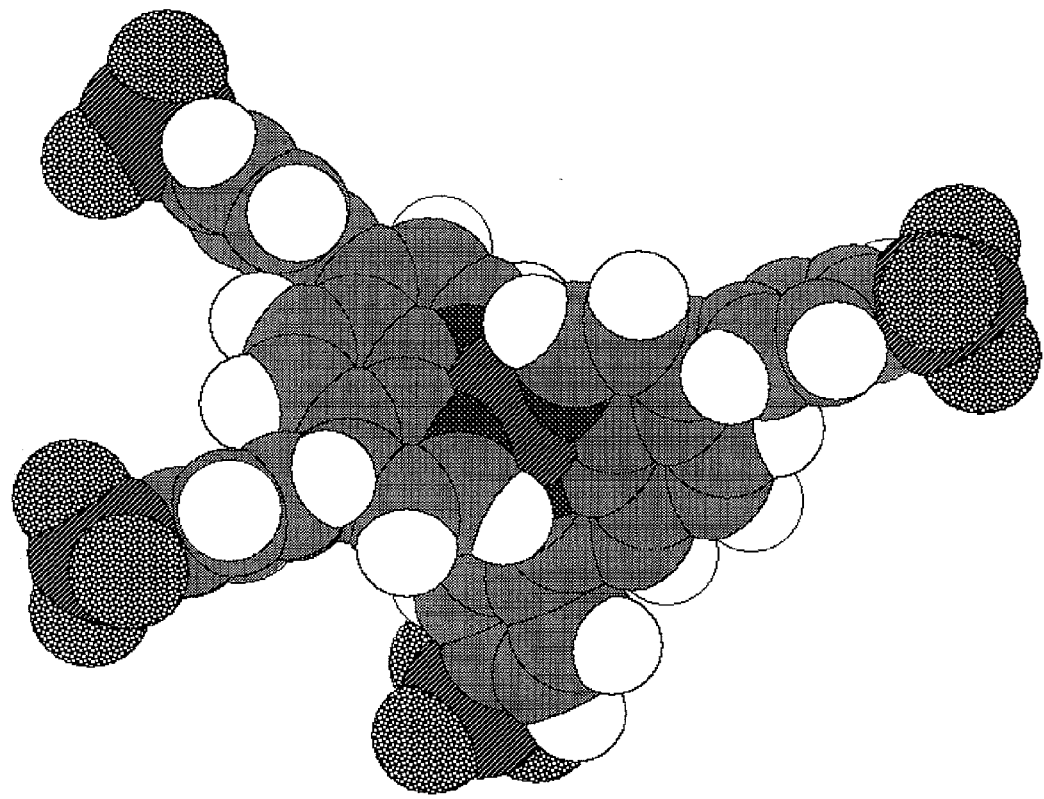
FIG. 2b shows a space-filling view
Figure 3A:
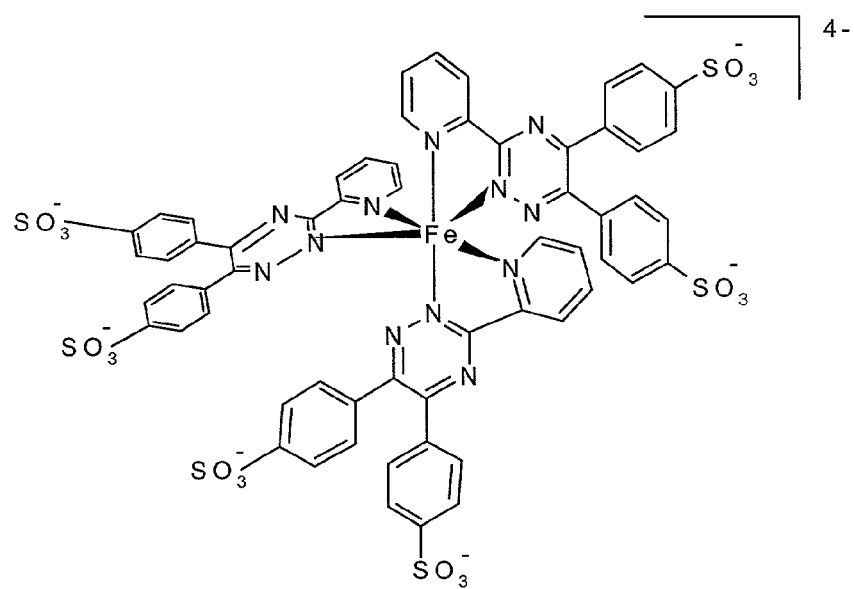
FIG. 3a shows the structural formula
Figure 3B:
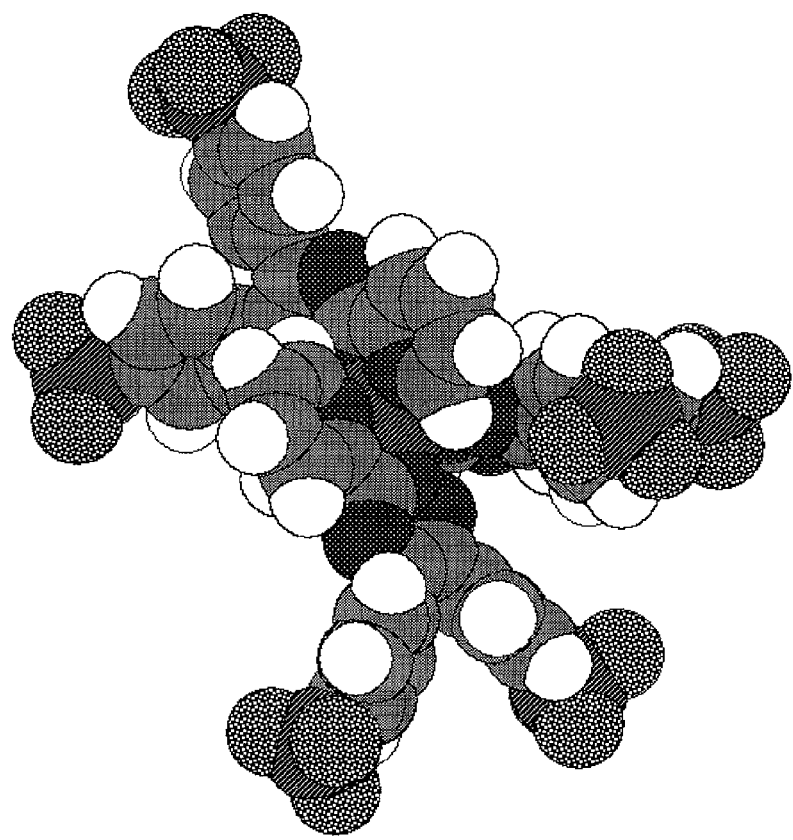
FIG. 3b shows a space-filling view

Metal complex pigments provided according to the present invention have (in contrast to, for example, the prior art organic pigment Orange G) a three-dimensional, e.g. tetrahedral or octahedral, coordination geometry, which for steric reasons greatly hinders adsorption of this type of molecule to a polar surfaces. In addition, the ligands can be substituted with ionic groups such as sulfonic or carboxyl groups, which further amplifies the hydrophilic or lipophobic properties. Indicator ions in aqueous systems are very hydrophilic due to their charge and the spherical hydrate shell and therefore also do not tend to adsorb on apolar surfaces.

Adsorption tests with various complexes suggested according to the present invention have shown that no significant adsorption occurs on the walls of the pipetting needle or tubing.

It is desirable that the liquid properties relevant for pipetting be changed as little is possible during the measurement process. The addition of an indicator salt, which reacts in the well of a microplate with a chromogen ligand, to the pipetting solution only influences the liquid properties slightly due to its good solubility. Influence of the physical properties is additionally reduced because the high extinction coefficient of the resulting complex permits the use of low initial concentrations of the indicator salt.

At least a stoichiometric quantity of the chromogen ligands must be present in the well before or after pipetting of the indicator salt solution. For reliable and rapid quantitative reaction, an excess of ligand can also be used. Any necessary buffer salts or redox active substances that convert the indicator ion into a suitable oxidation state are also present in the well. The actual pipetting procedure is therefore not influenced in any way, which makes this measurement system widely variable.

By complexing the indicator ion with a suitable auxiliary ligand, the indicator ion can be brought into solution in a suitable concentration in any desired solvent or mixture of solvents. For example, iron(III) ions can be brought into solution in nonpolar solvents with 2,4-pentane dione as an $[Fe(C_5H_7O_2)_3]$ complex. A wide palette of derivatives is accessible from 2,4-pentane dione, such as, for example, pentane-2,4-dione-1,5-diol, from which the solubility of the iron complex in any desired solvent can be adjusted. In the well, an auxiliary ligand is either quantitatively suppressed by a more chromogenic ligand and/or the complexed indicator ion is reduced by an oxidation number through a redox reaction, which allows the quantitative formation of a stronger complex with the chromogen ligand. Care must be taken that the absorption spectrum of the auxiliary ligands does not overlap with that of the chromophoric complex.

ELISA-Tests (ELISA=Enzyme-Linked Immuno Sorbent Assay) (cf. "PSCHYREMBEL Klinisches Wörterbuch" Walter de Gruyter GmbH & Co. KG, Berlin 1999, 258th edition) are now an integral part of clinical diagnostics and life science research. These tests frequently require one or more washing steps in the course of the test (cf. Lubert Stryer in "BIOCHEMISTRY", Freeman and Company, New York 1988, $3^{rd}$ Edition, Page 63). In practice, the reaction liquid is suctioned from the coated microplates. Subsequently, buffer solutions or test reagents are dispensed into the wells. These two functions are conventionally performed by a microplate washer. In the first step, the device acts as a suction element, while in the second step, the device is used as a dispenser. New commercially available devices (such as those from TECAN Austria, Untersbergstrasse 1a, 5082 Groedig, Austria) can dispense several different buffer solutions, which can be used individually or together. In addition to standard, art-recognized criteria for dispensing, microplate washers must fulfill additional specifications in regard to the residual volume (e.g. 2 μl at most) after suctioning in a well.

Microplates are preferably made of optically "perfect" materials. (If it were otherwise, positive absorption measurements would be obtained even with reagent "blank" solutions.) Microplates with flat bottoms and parallel walls are particularly preferably used. In microplates, particularly those with 384 or more wells, amplified meniscus formation can occur due to surface tension and liquid/wall interaction. If the menisci are irregular from well to well, different path lengths for the photometric measurements result, which negatively influences the reproducibility. Therefore, it is advisable to use microplates with low binding properties or otherwise modified surfaces to suppress the amplified meniscus formation.

In a first exemplary embodiment of quantitative measurements provided according to the methods of the invention, the system "$FeSO_4$ in aqueous solution with FerroZine®" was used; "FerroZine®" is the registered trademark of Hach Company, P.O. Box 389, Loveland, Colo. 80539 USA. The samples were pipetted both in the single pipetting mode (12 single pipettings each) and in the multipipetting mode (12 aliquots). 20, 100, 200, or 1000 individual droplets, (intended droplet volume=500 pl) respectively, were dispensed.

An aqueous 0.25 M $FeSO_4$ solution with FerroZine® and ammonium acetate buffer was used for producing a calibration curve. The resulting complex solution was stabilized with ascorbic acid. From this initial solution, measurement solutions were produced through dilutions that corresponded to pipetting volumes of 2.5 nl, 5.0 nl, 10.0 nl, 20.0 nl, 40.0 nl, and 80.0 nl in 200 µl. Twelve 200 µl aliquots of each of these measurement solutions were pipetted by hand into a microplate and the optical absorption and/or the optical densities (OD) were measured with a microplate photometry reader. The calibration curve was calculated through the measurement points by means of linear regression.

For the volume determinations, 100 µl of a 3.25 mM FerroZine® solution with ascorbic acid, buffered with ammonium acetate, was placed in the wells of a microplate. Ten nanoliters and 50 nl of a 0.25 M $FeSO_4$ solution stabilized with ascorbic acid was pipetted into this with a pipetting robot. The pipettings of 100 nl and 500 nl were performed with a 0.025 M $FeSO_4$ solution stabilized with ascorbic acid.

After pipetting, the volume was "topped up" to a total volume/well of 200 µl with demineralized water in the individual wells and the solutions were mixed well in the microplates by mechanical shaking. The optical absorption of the colored complex solution in the wells of a microplate was then measured in a microplate photometry reader and the volumes were calculated with reference to the calibration curve.

The results achieved with the system "$FeSO_4$ in aqueous solution with FerroZine®" are shown in the following tables 1 and 2:

TABLE 1

Single Pipetting Mode

| Intended volume | Average volume of the 12 single pipettings | ACC | CV |
|---|---|---|---|
| 10 nl | 9.7 nl | 3.0% | 2.9% |
| 50 nl | 48.0 nl | 4.0% | 1.2% |
| 100 nl | 101.8 nl | 1.8% | 1.5% |
| 500 nl | 497.5 nl | 0.5% | 1.5% |

TABLE 2

Multipipetting Mode

| Intended volume | Average volume of the 12 aliquots | ACC of the aliquots | CV of the aliquots |
|---|---|---|---|
| 10 nl | 9.8 nl | 2.0% | 1.4% |
| 50 nl | 48.1 nl | 3.8% | 2.5% |
| 100 nl | 99.3 nl | 0.7% | 4.0% |
| 500 nl | 509.0 nl | 1.8% | 2.8% |

In a second exemplary embodiment of quantitative measurements obtained according to the methods of the invention, the system "iron-tris(acetyl acetonate) in 100% dimethyl sulfoxide (DMSO) with FerroZine®" was used. The samples were pipetted both in the single pipetting mode (12 single pipettings each) and in the multipipetting mode (12 aliquots). Individual droplets (numbering 20, 100, 200, or 1000 individual droplets, respectively, with an intended droplet volume=400 pl) were dispensed. A 0.063 M iron-tris(acetyl acetonate) solution in pure DMSO was used for the calibration curve. From this initial solution, measurement solutions were produced, through dilutions with ammonium acetate buffer, ascorbic acid, and FerroZine®, which corresponded to pipetting volumes of 2.5 nl, 5.0 nl, 10.0 nl, 20.0 nl, 40.0 nl, and 80.0 nl in 200 µl . Twelve 200 µl aliquots of each of these measurement solutions were pipetted by hand into a microplate and the optical absorption and/or the optical densities (OD) were measured with a microplate photometry reader. The calibration curve was calculated through the measurement points by means of linear regression. For the volume determinations, 100 µl of a 3.25 mM FerroZine® solution with ascorbic acid buffered with ammonium acetate was placed in each of the wells of a microplate. Aliquots (8 nl, 40 nl, 80 nl, and 400 nl) of a 0.063 M iron-tris(acetyl acetonate) solution in pure DMSO were pipetted into this solution with the pipettor.

After pipetting, the volume was "topped up" to a total volume of 200 µl/well with demineralized water in the individual wells and the solutions were mixed well in the microplates by mechanical shaking. The optical absorption of the colored complex solution in the wells of the microplate was then measured in a microplate photometry reader and the volumes were calculated with reference to the calibration curve. The results achieved with the system "iron-tris(acetyl acetonate) in 100% dimethyl sulfoxide (DMSO) with FerroZine®" are shown in the following tables 3 and 4:

TABLE 3

Single Pipetting Mode

| Intended volume | Average volume of the 12 single pipettings | ACC | CV |
|---|---|---|---|
| 8 nl | 8.3 nl | 3.8% | 1.7% |
| 40 nl | 37.8 nl | 5.5% | 2.6% |
| 80 nl | 71.2 nl | 11.0% | 1.1% |
| 400 nl | 356.9 nl | 10.8% | 1.8% |

TABLE 4

Multipipetting Mode

| Intended volume | Average volume of the 12 aliquots | ACC of the aliquots | CV of the aliquots |
|---|---|---|---|
| 8 nl | 8.0 nl | 0.0% | 1.2% |
| 40 nl | 38.1 nl | 4.8% | 1.0% |
| 80 nl | 75.8 nl | 5.3% | 0.8% |
| 400 nl | 377.9 nl | 5.5% | 1.1% |

As these examples show, the methods of the invention provide a way to accurately and reproducibly dispense varying small amounts of liquid, and to have confidence in the amount dispensed. The method provided by the present invention actually permits the volume of a sample of a liquid to be determined and calibrated in the sub-microliter range, using the metal complex pigments and devices provided herein.

The present invention can also be used to determine the volume of a sample of a liquid and calibration in the sub-microliter range if anions are used as the indicator to stain the liquid (A). Complexing with a specific ligand also generates the staining of the sample in these cases. Examples of ligands for complexing of $F^-$, $Cl^-$ and/or $H_2PO_4^-$ ions in (dichloromethane) are described in the article by Miyamji et al. (2000, *Angew. Chem.* 112:1847-1849): anthraquinone functionalized systems covalently bonded at the β position, particularly calix[4]pyrrole-anthraquinone, have been shown to be very sensitive sensors for detecting these anions.

When performing the method according to the present invention, a polydentate molecule is preferably used as a ligand. Preferably, the polydentate ligand is a FerroZine®, bathophenanthroline-disulfonic acid disodium, bathocuproine-disulfonic acid disodium, or Chromazurol S. As mentioned before, a stoichiometric quantity of the specific chromogenic ligands must be present for reliable and rapid quantitative reaction. However, an excess of the specific chromogenic ligands, e.g., in the form of polydentate molecules, can also be used.

What is claimed is:

1. A method for determining the volume of a dispensed liquid sample, wherein the sample liquid comprises a fixed concentration of indicator ions comprising the steps of:

providing a diluent in a container, the diluent comprising polydentate chromogenic ligands of one type;

dispensing a volume of the sample liquid into the diluent, thereby forming complexes of the polydentate chromogenic ligands with the indicator ions, which complexes are chromophoric indicators for staining the resulting mixture;

measuring the optical absorption of the stained mixture in the container; and determining the volume of the dispensed liquid sample by correlating the measured optical absorption of the stained mixture with the optical absorption of a test sample that has an exactly defined concentration of the same chromophoric indicator, and wherein the chromophoric indicator is a colored complex that has a three-dimensional coordination geometry, which greatly hinders adsorption of this type of molecule to apolar surfaces.

2. A method for determining a residual volume of a liquid in a sample holder comprising the steps of:

providing a liquid in a sample holder comprising a fixed concentration of indicator ions;

removing a volume of the liquid from the sample holder;

adding a diluent comprising polydentate chromogenic ligands of one type to the liquid remaining in the sample holder to form the complexes of the polydentate chromogenic ligands with the indicator ions, which complexes are chromophoric indicators for staining the resulting mixture;

measuring the optical absorption of the stained mixture in the sample holder; and determining the residual volume of the liquid by correlating the measured optical absorption of the stained mixture in the sample holder with the optical absorption of a test sample that has an exactly defined concentration of the same chromophoric indicator, and wherein the chromophoric indicator is a colored complex that has a three-dimensional coordination geometry, which greatly hinders adsorption of this type of molecule to apolar surfaces.

3. A method for determining the volume of a dispensed liquid sample, comprising the steps of:

providing a diluent in a container;

dispensing a volume of a sample liquid comprising a chromophoric indicator that stains the sample liquid to form a mixture in the container;

measuring the optical absorption of the stained mixture in the container; and determining the volume of the dispensed liquid sample by correlating the measured optical absorption of the stained mixture with the optical absorption of a test sample that has an exactly defined concentration of the same chromophoric indicator, wherein the chromophoric indicator to stain the sample liquid is a colored complex that is formed by complexing indicator ions with specific polydentate chromogenic ligands with a three-dimensional coordination geometry which greatly hinders adsorption of this type of molecule to apolar surfaces.

4. A method for determining a residual volume of a liquid in a sample holder comprising the steps of:

providing a liquid in a sample holder comprising a chromophoric indicator;

removing a part of the liquid in the sample holder;

adding a diluent to the residual volume of the liquid in the sample holder;

measuring the optical absorption of the diluted residual volume of the liquid; and determining the residual volume of the liquid in the sample holder by correlating the measured optical absorption of the mixture with the optical absorption of a test sample that has an exactly defined concentration of the same chromophoric indicator, wherein the chromophoric indicator to stain the liquid is formed by complexing indicator ions with specific polydentate chromogenic ligands with a three-dimensional coordination geometry, which greatly hinders adsorption of this type of molecule to apolar surfaces.

5. The method according to claim 1 or 2, wherein, prior to dispensing the liquid sample, a compensating volume is provided in the container as part of the diluent.

6. The method of claim 1 wherein the solution from which liquid is dispensed further comprises complexes composed of one type of auxiliary ligands and indicator ions for improving the solubility of the indicator ions in the solution.

7. The method of claim 2 wherein the liquid in the sample holder further comprises complexes composed of one type of auxiliary ligands and indicator ions for improving the solubility of the indicator ions in the liquid.

8. The method according to claim 1 or 2, wherein the polydentate chromogenic ligand is added to the diluent in excess.

9. The method according to claim 1 or 3, wherein after dispensing the liquid sample into the container, a supplementary volume is added to this container as part of the diluent.

10. The method according to claim 1, 2, 3, or 4, wherein the indicator ions for complexing with the polydentate chromogenic ligands comprise metal ions.

11. The method according to claim 10, wherein the metal ions are $Fe^{++}$, $Fe^{+++}$, mixtures of $Fe^{++}$ and $Fe^{+++}$, or $Cu^{++}$.

12. The method according to claim 1, 2, 3, or 4, wherein indicator ions for complexing with the polydentate chromogenic ligands are anions.

13. The method according to claim 12, wherein the anions are $F^-$, $Cl^-$, or $H_2PO_4^-$.

14. The method according to claim 10, wherein metal ions which cannot be quantitatively complexed with the polydentate chromogenic ligands are reduced or oxidized to indicator ions prior to complexing with the polydentate chromogenic ligands.

15. The method according to claim 14, wherein the metal ions are reduced with hydroxyl amine hydrochloride, a tartrate salt, or ascorbic acid or the metal ions are oxidized with hexacyanoferrate or elementary bromine.

16. The method of claim 1, 2, 3, or 4, wherein the polydentate chromogenic ligand is FerroZine®, bathophenanthroline-disulfonic acid disodium, bathocuproinedisulfonic acid disodium or Chromazurol S.

17. The method according to claim 6 or 7, wherein the auxiliary ligands are β-diketones.

18. The method of claim 17, wherein the β-diketones are acetyl acetonate or pentane-2,4-dione-1,5-diol.

19. The method of claim 12, wherein the chromogenic ligands are anthraquinone functionalized systems covalently bonded at the β2 position.

20. The method of claim 19, wherein the anthraquinone functionalized system covalently bonded at the β position is calix[4]pyrrole-anthraquinone.

21. The method according to claim 16, wherein the chromophoric indicator comprises substituted ionic groups that further amplify the hydrophilic properties of the chromophoric indicator.

22. The method according to claim 1 or 2, wherein metal ions, which cannot be quantitatively complexed with the polydentate chromogenic ligands, are complexed with auxiliary ligands thereby improving their solubility in a liquid, a sample of the liquid is dispensed into the diluent, wherein the diluent is an existing reaction solution that comprises polydentate chromogenic ligands and a reducing or oxidizing agent, wherein a reducing or oxidizing agent is reducing or oxidizing the metal ions to indicator ions which are then complexed with the polydentate chromogenic ligands under color development.

23. The method according to claim 6 or 7, in which the metal ions that have been complexed with auxiliary ligands are mixed with the diluent containing polydentate chromogenic ligands, wherein the indicator ions are then complexed with the polydentate chromogenic ligands under color development while suppressing the auxiliary ligands.

* * * * *